US008204698B2

(12) United States Patent
Li et al.

(10) Patent No.: US 8,204,698 B2
(45) Date of Patent: Jun. 19, 2012

(54) METHOD FOR DETERMINING STRUCTURAL PARAMETERS OF COMPOSITE BUILDING PANELS

(75) Inventors: Alfred C. Li, Naperville, IL (US); Arthur Kennedy, Crystal Lake, IL (US); Kristin McKeever, legal representative, Queensbury, NY (US)

(73) Assignee: United States Gypsum Company, Chicago, IL (US)

( * ) Notice: Subject to any disclaimer, the term of this patent is extended or adjusted under 35 U.S.C. 154(b) by 343 days.

(21) Appl. No.: 12/544,707

(22) Filed: Aug. 20, 2009

(65) Prior Publication Data

US 2011/0046898 A1 Feb. 24, 2011

(51) Int. Cl.
*G01L 1/00* (2006.01)
(52) U.S. Cl. .............. 702/41; 702/42; 702/43; 702/127; 52/344
(58) Field of Classification Search ...................... 702/41
See application file for complete search history.

(56) References Cited

U.S. PATENT DOCUMENTS

| | | | |
|---|---|---|---|
| 3,003,351 A | 10/1961 | Ziegler et al. | |
| 3,714,820 A | 2/1973 | Strickler et al. | |
| 4,538,462 A | 9/1985 | Hartog et al. | |
| 4,565,041 A | 1/1986 | Wendt | |
| 4,708,020 A | 11/1987 | Lau et al. | |
| 4,719,583 A | 1/1988 | Takafuji et al. | |
| 5,048,320 A | 9/1991 | Mitsuhashi et al. | |
| 5,922,447 A | 7/1999 | Baig | |
| 6,347,542 B1 | 2/2002 | Larsson et al. | |
| 6,391,958 B1 | 5/2002 | Luongo | |
| 6,620,487 B1 | 9/2003 | Tonyan et al. | |
| 6,816,791 B2 | 11/2004 | Myers et al. | |
| 6,841,232 B2 | 1/2005 | Tagge et al. | |
| 7,017,422 B2 | 3/2006 | Heyman et al. | |
| 7,066,007 B2 | 6/2006 | Ziegler et al. | |
| 7,204,153 B2 | 4/2007 | Phipps | |
| 7,244,304 B2 | 7/2007 | Yu et al. | |
| 2004/0028956 A1 | 2/2004 | Savoly et al. | |
| 2004/0045481 A1 | 3/2004 | Sethuraman et al. | |
| 2004/0092624 A1 | 5/2004 | Tagge et al. | |
| 2004/0154264 A1 | 8/2004 | Colbert | |
| 2005/0103119 A1 | 5/2005 | Shtakelberg et al. | |

(Continued)

FOREIGN PATENT DOCUMENTS

WO WO 2005061772 A1 * 7/2005

OTHER PUBLICATIONS

Kazys et al., Ultrasonic Non-Destructive On-Line Estimation of the Tensile Stiffness of a Running Paper Web, NDT&E International 34 (2001) 259-267.*

(Continued)

*Primary Examiner* — Jonathan C Teixeira Moffat
*Assistant Examiner* — Timothy H Hwang
(74) *Attorney, Agent, or Firm* — Greer, Burns & Brain, Ltd.; David Janci; Philip T. Petti

(57) ABSTRACT

A method of determining face paper properties of wallboard including providing a core strength value of the wallboard, determining a required nail pull value based the wallboard specifications and calculating a face paper stiffness value based on the provided core strength value and the determined nail pull value. The method includes displaying the calculated face paper stiffness value on a display device.

9 Claims, 4 Drawing Sheets

U.S. PATENT DOCUMENTS

| | | |
|---|---|---|
| 2006/0162839 A1 | 7/2006 | Seki et al. |
| 2007/0048490 A1 | 3/2007 | Yu et al. |
| 2007/0054102 A1* | 3/2007 | Baig .................... 428/292.1 |
| 2007/0122604 A1* | 5/2007 | Wang et al. ............ 428/294.7 |
| 2008/0176053 A1* | 7/2008 | Miller et al. ............ 428/220 |

OTHER PUBLICATIONS

C. Fellers et al., Paper: Strength and Stiffness, Encyclopedia of Material—Science and Technology, vols. 1-11 (2001) 6720-6725.*

Glossary of Terms, http://www.temap.com/prp/glossary.html.*

* cited by examiner

FIG. 1

| Paper Roll ID | Face Paper Stiffness (kN/m) | Core Strength (psi) | Tested Nail Pull Value | Predicted Nail Pull Value | Average Tested Nail Pull Value | Average Predicted Nail Pull Value |
|---|---|---|---|---|---|---|
| Sample No. 1 | 3099 | 359 | 70 | 67 | 71 | 67 |
| Sample No. 1 | 3099 | 350 | 69 | 66 | | |
| Sample No. 1 | 3099 | 358 | 68 | 67 | | |
| Sample No. 1 | 3099 | 392 | 73 | 70 | | |
| Sample No. 1 | 3099 | 374 | 74 | 68 | | |
| Sample No. 1 | 3099 | 360 | 70 | 67 | | |
| Sample No. 2 | 3211 | 451 | 76 | 76 | 73 | 76 |
| Sample No. 2 | 3211 | 440 | 70 | 75 | | |
| Sample No. 2 | 3211 | 459 | 73 | 77 | | |
| Sample No. 2 | 3211 | 460 | 74 | 77 | | |
| Sample No. 3 | 2995 | 450 | 70 | 74 | 72 | 74 |
| Sample No. 3 | 2995 | 466 | 76 | 76 | | |
| Sample No. 3 | 2995 | 453 | 71 | 75 | | |
| Sample No. 3 | 2995 | 441 | 73 | 73 | | |
| Sample No. 3 | 2995 | 454 | 70 | 75 | | |
| Sample No. 3 | 2995 | 433 | 74 | 73 | | |
| Sample No. 4 | 2988 | 541 | 82 | 83 | 83 | 82 |
| Sample No. 4 | 2988 | 550 | 82 | 83 | | |
| Sample No. 4 | 2988 | 552 | 87 | 84 | | |
| Sample No. 4 | 2988 | 571 | 85 | 85 | | |
| Sample No. 4 | 2988 | 533 | 87 | 82 | | |
| Sample No. 4 | 2988 | 492 | 75 | 78 | | |
| Sample No. 5 | 3310 | 476 | 79 | 80 | 82 | 81 |
| Sample No. 5 | 3310 | 492 | 85 | 81 | | |
| Sample No. 5 | 3310 | 532 | 84 | 85 | | |
| Sample No. 5 | 3310 | 502 | 83 | 82 | | |
| Sample No. 5 | 3310 | 488 | 82 | 81 | | |
| Sample No. 5 | 3310 | 483 | 82 | 80 | | |
| Sample No. 6 | 3345 | 474 | 75 | 80 | 80 | 79 |
| Sample No. 6 | 3345 | 481 | 82 | 80 | | |
| Sample No. 6 | 3345 | 457 | 81 | 78 | | |
| Sample No. 6 | 3345 | 462 | 79 | 79 | | |
| Sample No. 6 | 3345 | 470 | 81 | 79 | | |
| Sample No. 6 | 3345 | 472 | 80 | 80 | | |
| Sample No. 6 | 3345 | 456 | 80 | 78 | | |
| Sample No. 7 | 3262 | 450 | 72 | 77 | 74 | 77 |
| Sample No. 7 | 3262 | 447 | 74 | 77 | | |
| Sample No. 7 | 3262 | 473 | 74 | 79 | | |
| Sample No. 7 | 3262 | 488 | 75 | 80 | | |
| Sample No. 7 | 3262 | 448 | 72 | 77 | | |
| Sample No. 7 | 3262 | 423 | 77 | 74 | | |
| Sample No. 8 | 3313 | 444 | 74 | 77 | 80 | 80 |
| Sample No. 8 | 3313 | 509 | 84 | 83 | | |
| Sample No. 8 | 3313 | 503 | 83 | 82 | | |
| Sample No. 8 | 3313 | 485 | 82 | 80 | | |
| Sample No. 8 | 3313 | 477 | 81 | 80 | | |
| Sample No. 8 | 3313 | 495 | 80 | 81 | | |
| Sample No. 8 | 3313 | 470 | 79 | 79 | | |
| Sample No. 9 | 3345 | 461 | 84 | 79 | 81 | 79 |
| Sample No. 9 | 3345 | 476 | 82 | 80 | | |
| Sample No. 9 | 3345 | 456 | 77 | 78 | | |
| Sample No. 9 | 3345 | 477 | 81 | 80 | | |
| Sample No. 9 | 3345 | 483 | 83 | 81 | | |
| Sample No. 10 | 3169 | 447 | 78 | 76 | 77 | 77 |
| Sample No. 10 | 3169 | 465 | 78 | 77 | | |
| Sample No. 10 | 3169 | 463 | 77 | 77 | | |
| Sample No. 10 | 3169 | 465 | 78 | 77 | | |
| Sample No. 10 | 3169 | 477 | 80 | 78 | | |
| Sample No. 10 | 3169 | 472 | 74 | 78 | | |
| Sample No. 10 | 3169 | 469 | 76 | 78 | | |
| Sample No. 11 | 3218 | 483 | 79 | 79 | 81 | 80 |
| Sample No. 11 | 3218 | 504 | 79 | 81 | | |
| Sample No. 11 | 3218 | 498 | 83 | 81 | | |
| Sample No. 11 | 3218 | 487 | 83 | 80 | | |
| Sample No. 11 | 3218 | 477 | 81 | 79 | | |
| Sample No. 11 | 3218 | 481 | 82 | 79 | | |
| Sample No. 11 | 3218 | 484 | 82 | 80 | | |

FIG. 6

| Nail Pull Model | Core Strength (psi) | | | |
|---|---|---|---|---|
| TSIA (kNm/g) | 400 | 450 | 500 | 550 |
| | Face Paper Weight (lb/MSF) Required to Achieve 77lb$_f$ Nail Pull | | | |
| 14 | 55 | 48 | 41 | 34 |
| 15 | 52 | 45 | 38 | 32 |
| 16 | 48 | 42 | 36 | 30 |
| 19.5 | 40 | 35 | 29 | 24 |

METHOD FOR DETERMINING STRUCTURAL PARAMETERS OF COMPOSITE BUILDING PANELS

FIELD OF THE INVENTION

This invention relates to composite building panels. More specifically, it relates to a method for determining structural parameters of gypsum wallboard.

BACKGROUND OF THE INVENTION

Composite building panels, such as gypsum wallboard, are well known for interior wall and ceiling construction. Some of the main advantages of wallboard over other materials is that wallboard is less expensive, a fire retardant and easy to work with in construction applications. In construction, wallboard is typically secured to wood or metal supports of framed walls and ceilings using fasteners such as nails or screws. Because wallboard is relatively heavy, it must be strong enough to prevent the fasteners from pulling through the wallboard and causing the wallboard to loosen or fall away from the supports.

Nail pull is an industry measure of the amount of force required for wallboard to be pulled away from the associated support and over the head of such a fastener. Preferable nail pull values for wallboard are in the approximate range of between 65-85 pounds of force. Nail pull is a measure of a combination of the wallboard core strength, the face paper strength and the bond between the face paper and the core. Nail pull tests are performed in accordance with the American Society for Testing Materials (ASTM) standard C473-00 and utilize a machine that pulls on a head of a fastener inserted in the wallboard to determine the maximum force required to pull the fastener head through the wallboard. Because the nail pull value is an important measure of wallboard strength, minimum required nail pull values have been established for wallboard. Accordingly, manufacturers produce wallboard that meets or exceeds the minimum required nail pull values.

To ensure that wallboard meets the required nail pull values, conventional wallboard manufacturers adjust the structural parameters of the wallboard. Specifically, manufacturers typically adjust the face paper weight of wallboard having a known core strength value to meet the required nail pull value. During manufacturing, wallboard is tested to determine if it meets the required nail pull value. If the tested nail pull value of the wallboard is less than the required nail pull value, manufacturers increase the face paper weight on the wallboard. This process is repeated until the required nail pull value is met.

Such a process is inaccurate and commonly causes the tested nail pull values to exceed the required nail pull values due to excess face paper weight added to the wallboard. Also, the excess face paper adds weight to wallboard and thereby increases manufacturing and shipping costs of wallboard. Further, there is the likelihood of wasting time and material until the desired nail pull values are achieved on the wallboard production line.

Thus, there is a need for an improved technique of adjusting wallboard manufacturing systems to produce wallboard that meets specified nail pull values.

SUMMARY OF THE INVENTION

These, and other problems readily identified by those skilled in the art, are solved by the present method of determining structural properties of composite building panels such as wallboard.

The present method is designed for determining structural parameters of gypsum wallboard prior to manufacturing to reduce manufacturing and shipping costs as well as significantly reduce manufacturing time.

More specifically, the present method determines structural parameters of wallboard and includes providing a core strength value of the wallboard, determining a required nail pull value and calculating a face paper stiffness value based on the provided core strength value and the determined nail pull value. The calculated face paper stiffness value is displayed on a display device for use by a manufacturer.

In another embodiment, a method of manufacturing wallboard includes determining a required nail pull value, providing a core strength value of the wallboard and determining a face paper stiffness value based on the required nail pull value and the provided core strength value. The method includes determining a face paper weight based on the determined face paper stiffness value, selecting a face paper type based on the determined face paper weight and producing the wallboard using the selected face paper type and the provided core strength value.

Determining the structural parameters prior to manufacturing enables manufacturers to save significant manufacturing and shipping costs by eliminating excess face paper weight that is typically added to wallboard to meet required nail pull values. Additionally, a significant amount of manufacturing time is saved because less time is needed to test the manufactured wallboard to determine the face paper weight needed to meet required nail pull values. Furthermore, the structural integrity and strength of wallboard is maintained, even though the additional weight and stress added by the excess face paper is reduced.

DETAILED DESCRIPTION OF THE DRAWINGS

FIG. 1 is a table illustrating a comparison between measured nail pull data and predicted nail pull data for the same types of wallboard using different face papers.

FIG. 6 is a table identifying certain face paper weight values and Tensile Strength Index Area (TSIA) values needed to achieve a required nail pull value of 77 $lb_f$ at different core strength values based on the graph of FIG. 5.

DETAILED DESCRIPTION OF THE INVENTION

Figure 2:
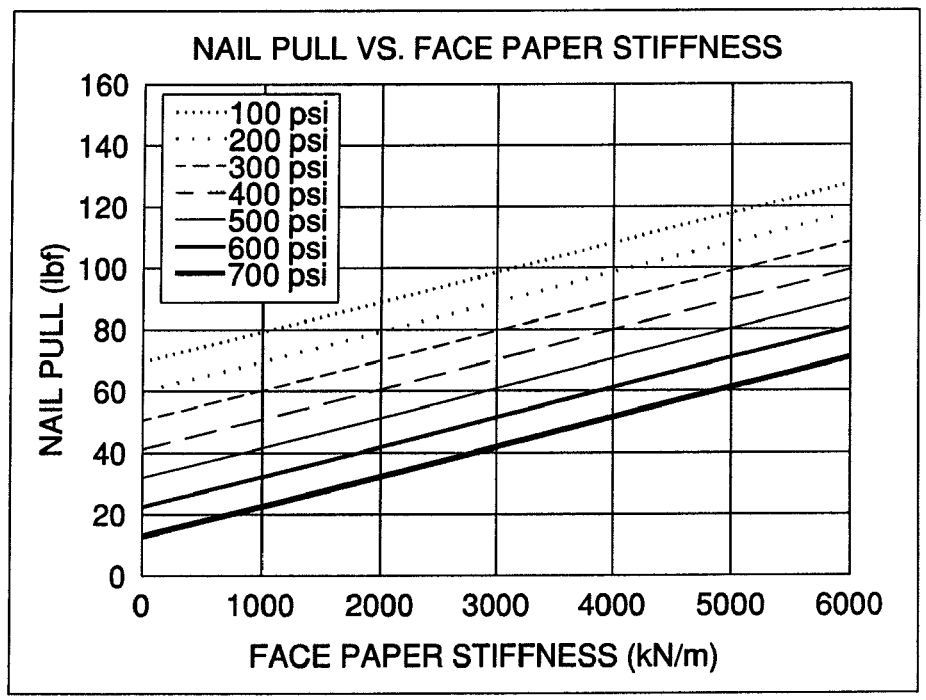
FIG. 2 is a graph illustrating nail pull as a function of the face paper stiffness at different core strength values.

Nail pull values are critical to the strength and usefulness of gypsum wallboard. If a nail pull value for a particular wallboard is too low, the fastener holding the wallboard on a frame or other support can pull through the wallboard and cause the wallboard to crack, break or fall from the frame or support. Alternatively, if nail pull values are too high (i.e., significantly exceed required nail pull values), wallboard production resources are inefficiently applied and money is wasted during manufacturing.

A problem in gypsum wallboard manufacturing is how to accurately determine the face paper weight that correlates to a required nail pull value for wallboard and a way that more efficiently utilizes manufacturing and shipping costs, as well as manufacturing time. As stated above, wallboard manufacturers perform tests on wallboard to determine if it meets a required nail pull value. If the required nail pull value is not met, manufacturers typically increase the face paper weight of the wallboard. These steps are repeated until the required nail pull value of the wallboard is met. This process is not accurate and often causes the wallboard to have excess face paper, which increases the overall weight of wallboard and thereby increases manufacturing and shipping costs as well as manufacturing time.

The present method determines a face paper weight, or alternatively a face paper stiffness value, for wallboard prior to manufacturing that meets the required nail pull value. The method utilizes the following equation that correlates a required nail pull value with the face paper stiffness value and the core strength value of wallboard. The equation is as follows:

$$\text{Nail Pull (lb}_f) = a \text{ (lb}_f) + [b \text{ (lb}_f/(kN/m)) \times (\text{face paper stiffness (kN/m)})] + [c \text{ (lb}_f/psi) \times (\text{core strength (psi)})] \quad (1)$$

where a=4.2126759, b=0.009490606731, c=0.092421774 are constants determined from testing data that best fit the data shown in FIG. 1.

Prior to manufacturing, the core strength value of wallboard is determined and the required nail pull value is determined for the wallboard to be manufactured (i.e., quarter inch, half inch, etc.). These values are entered in Equation (1) above to determine the face paper stiffness value of the wallboard. For example, the face paper stiffness value for wallboard having a core strength value of 400 pounds per square inch (psi) and a required nail pull value of 77 pound-force (lb.sub.f) is as follows:

$$77 \text{ (lb}_f) = (4.2126759 \text{ (lb}_f) + [((0.009490606731) \text{ (lb}_f/(kN/m)) \times (\text{face paper stiffness (kN/M)})] + [((0.092421774) \text{ (lb}_f/psi)) \times (400 \text{ psi})]$$

where the face paper stiffness value=3774 kiloNewton/meter (kN/m).

The face paper stiffness value is a product of the face paper weight and the Tensile Stiffness Index Area (TSIA) value as shown in the following equation:

$$\text{Face Paper Stiffness (kN/m)} = \text{Face Paper Weight (g/m}^2) \times \text{TSIA (kNm/g)} \quad (2)$$

Using the above example, the Face Paper Weight for the above wallboard having a core strength value of 400 psi, a required nail pull value of 77 lb$_f$ and a TSIA of 26 kiloNewton-meter/gram (kNm/g) is as follows:

$$\text{Face Paper Weight (g/m}^2) = \text{Face Paper Stiffness (kN/m)} / TSIA \text{ (kNm/g)}$$
$$= (3774 \text{ kN/m}) / (26 \text{ kNm/g})$$
$$= 145.15 \text{ gram/meter squared (g/m}^2)$$

In the above equation, the TSIA value is a measurement of the normalized face paper stiffness in all directions on the wallboard. Specifically, an ultrasonic Tensile Stiffness Orientation (TSO®) tester machine measures the Tensile Stiffness Index (TSI) in all directions on the wallboard to determine the TSIA. The stiffer the face paper, the larger the TSIA values. The approximate range of TSIA values for wallboard is 12 to 20 kNm/g.

The face paper stiffness value and TSIA value are used to determine the weight of the face paper that is needed to achieve the required nail pull value for wallboard having a designated core strength value. The calculation for determining the face paper weight is therefore a two-step process of first determining the face paper stiffness and then determining the face paper weight for the wallboard being manufactured.

Equations (1) and (2) are preferably stored in a memory of a computer, personal data assistant or other suitable device. The required nail pull values, core strength values and constants are also stored in the memory in a database or other searchable data format. The memory may be a read-only memory (ROM), random access memory (RAM), compact disk read-only memory (CD ROM) or any other suitable memory or memory device. A user or manufacturer inputs the required nail pull value and designated core strength value for the wallboard into the computer using a keyboard or other suitable input device. Alternatively, the required nail pull value and designated core strength value for the wallboard may be downloaded and stored in a file or folder in the memory. A processor, such as a microprocessor or a central processing unit (CPU), calculates the face paper weight for the wallboard using Equations (1) and (2), the inputted nail pull value and the inputted core strength value. The calculated face paper weight, or alternatively the face paper stiffness value, is displayed to a user on a display device such as a computer screen, monitor or other suitable output device or printed out by a printer. The user uses the calculated face paper weight to select the face paper or face paper type that is to be adhered to the core during manufacturing of the wallboard. The face paper selected using the present method typically reduces the face paper stiffness and weight needed to achieve the required nail pull value compared to conventional wallboard production techniques. Additionally, the present method reduces the overall weight of the manufactured wallboard, which reduces manufacturing and shipping costs. The present method also significantly reduces the manufacturing time associated with producing the wallboard because the intermediate testing of the wallboard to determine if the wallboard meets required nail pull values is no longer necessary.

FIG. 1 is a table that illustrates a comparison between the measured nail pull data and the predicted nail pull data for different wallboard (sample nos. 1-11) using Equation (1). As shown in the table, the predicted average nail pull data using Equation (1) correlates well with the tested or measured average nail pull data of the wallboard. For example, the average tested or measured nail pull value for sample no. 4 was 83 compared to the predicted nail pull value of 82 using Equation (1). Similarly, the tested or measured average nail pull values for sample no. 5, sample no. 6 and sample no. 11 also differ by a value of one compared to the corresponding average predicted nail pull value using Equation (1) (e.g., 82,81; 80,79; 81,80). Furthermore, the predicted nail pull values for sample no. 8 and sample no. 10 wallboard were exactly the same as the corresponding tested or measured nail pull values (e.g., 80,80 and 77,77). Thus, the present method predicts the nail pull values for wallboard with a high degree of accuracy.

Equations (1) and (2) can also be used to predict different structural parameters or values of wallboard to enhance the manufacturing process.

For example, from Equation (1), nail pull data can be expressed as a linear function of the face paper stiffness at different core strength values ranging from 100 psi to 700 psi, as shown in FIG. 2. The core strength value of wallboard varies based on the type of wallboard being manufactured.

The typical range of core strength values for the wallboard considered in FIG. 1 is 400 to 500 psi.

Figure 3:
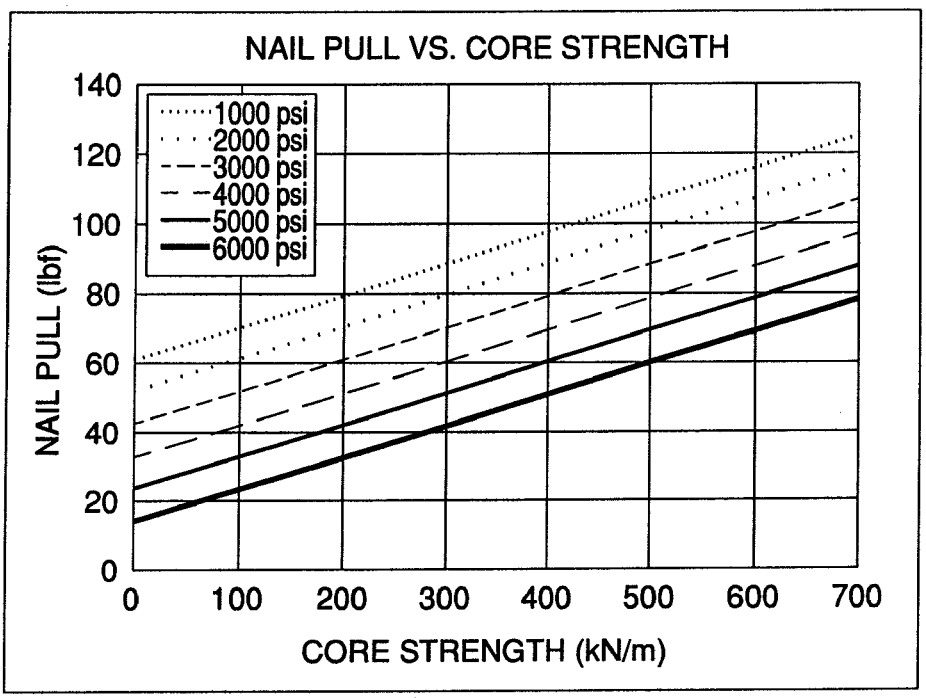
FIG. 3 is a graph illustrating nail pull as a function of the core strength at different face paper stiffness values.

The nail pull data can also be plotted as a linear function of the core strength with the face paper stiffness values ranging from 1000 kN/m to 6000 kN/m, as shown in FIG. 3. Preferably, the face paper stiffness values range from 2500 to 4000 kN/m for wallboard. In FIGS. 2 and 3, it is apparent that increasing either the face paper stiffness value or the core strength value of wallboard increases the nail pull value.

Figure 4:
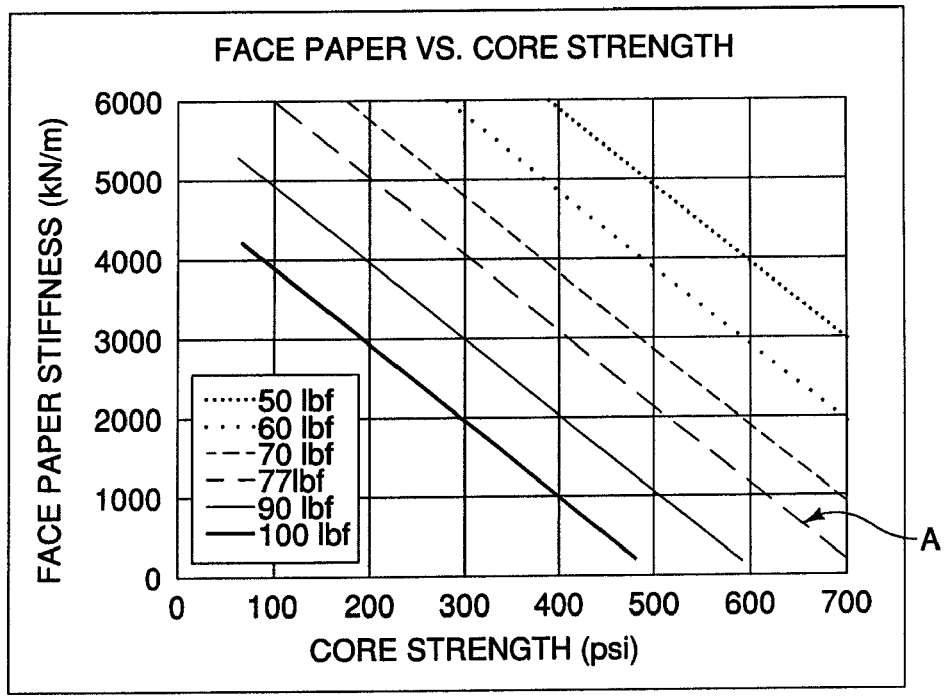
FIG. 4 is a graph illustrating the relationship between the face paper stiffness and the core strength at different required nail pull values.

FIG. 4 shows a plot of the face paper stiffness value as a function of the core strength value at various different nail pull values. Specifically, line "A" illustrates the relationship between the face paper stiffness values and the core strength values at a target minimum nail pull value of 77 $lb_f$. The ratio of the empirical constants c/b (=9.74) in Equation (1) provides the change in the face paper stiffness values with respect to the change in the core strength values. To maintain the required nail pull value of 77 $lb_f$, a reduction (or increase) of 100 psi in the core strength values corresponds to a 974 kN/m increase (or decrease) in the face paper stiffness values. Furthermore using Equation (2), a higher face paper stiffness value can be accomplished by increasing either the face paper weight or the TSIA.

Figure 5:
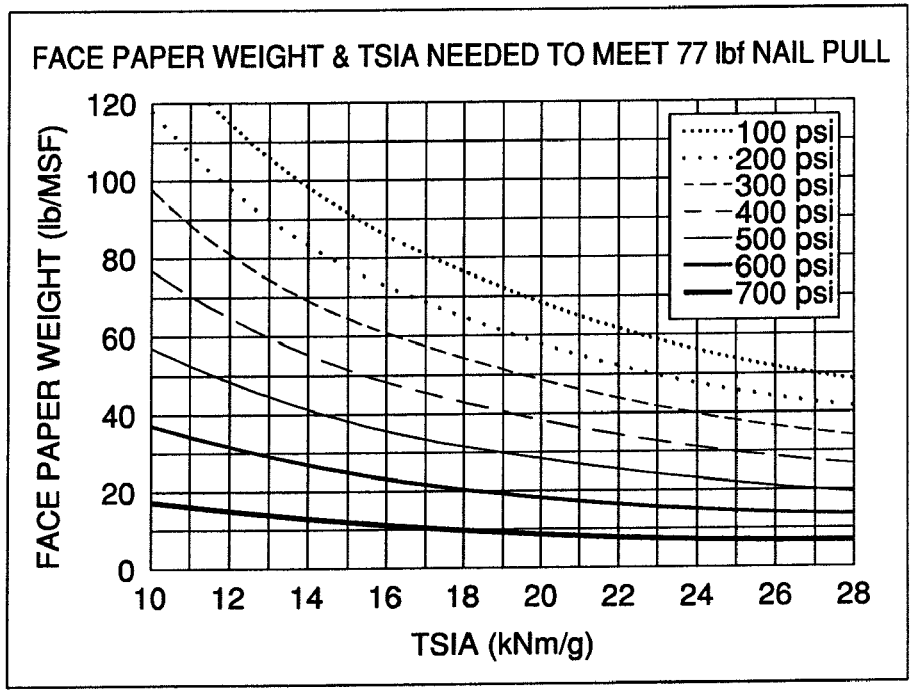
FIG. 5 is a graph illustrating the relationship between the face paper weight and the Tensile Strength Index Area (TSIA) values needed to achieve a required nail pull value of 77 $lb_f$ at different core strength values.

FIG. 5 illustrates the relationship between the face paper weight and the TSIA that meets a required nail pull value of 77 $lb_f$. The face paper weight requirements for different TSIA values are summarized in the table shown in FIG. 6. Note that increasing the TSIA value from 14 to 19.5 kNm/g tends to reduce the required face paper weight by an average of 28%, while maintaining the required nail pull value of 77 $lb_f$.

The present method enables wallboard manufacturers to determine important parameters and properties of the wallboard prior to manufacturing such as the face paper weight needed to achieve a required nail pull value. Obtaining these parameters prior to manufacturing helps to significantly reduce manufacturing time, as well as manufacturing costs and shipping costs. The present method also allows manufacturers to maintain the structural integrity and performance of wallboard without adding face paper weight on wallboard.

While several particular embodiments of the present method have been shown and described, it will be appreciated by those skilled in the art that changes and modifications may be made thereto without departing from the invention in its broader aspects and as set forth in the following claims.

What is claimed is:

1. A method of determining structural parameters of wallboard, comprising:
   providing a core strength of the wallboard;
   determining a required nail pull value based on a thickness of the wallboard type;
   calculating by a processor a face paper stiffness value based on said provided core strength value and said determined nail pull value, wherein said face paper stiffness value is based on the following equation:

Nail Pull ($lb_f$)=$a$ ($lb_f$)+[$b$ ($lb_f$/(kN/m))]×(face paper stiffness (kN/m))]+[$c$ ($lb_f$/psi)×(core strength (psi))] wherein $a$=4.2126759, $b$=0.009490606731 and $c$=0.092421774;

displaying said calculated face paper stiffness value on a display device; and
   selecting a face paper type for the wallboard based on said displayed face paper stiffness value.

2. The method of claim 1, wherein said core strength value is in the approximate range of 400 to 500 psi.

3. The method of claim 1, further including calculating a face paper weight by dividing said face paper stiffness value by a Tensile Stiffness Index Area (TSIA) value.

4. The method of claim 3, further including selecting a type of face paper based on said calculated face paper weight.

5. The method of claim 3, wherein said TSIA value is in the range of 12 to 26 kNm/g.

6. A method of manufacturing wallboard comprising:
   determining a required nail pull value based on the wallboard type;
   providing a core strength value of the wallboard;
   determining by a processor a face paper stiffness value based on said determined required nail pull value and said provided core strength value, wherein said face paper stiffness value is based on the following equation:

Nail Pull ($lb_f$)=$a$ ($lb_f$)+[$b$ ($lb_f$/(kN/m))]×(face paper stiffness (kN/m))]+[$c$ ($lb_f$/psi)×(core strength (psi))] wherein $a$=4.2126759, $b$=0.009490606731 and $c$=0.092421774;

determining, by the processor a face paper weight based on said calculated face paper stiffness value and displaying said determined face paper weight;
   selecting a face paper type based on said displayed face paper weight; and
   producing the wallboard based using said selected face paper type and said provided core strength value.

7. The method of claim 6, wherein determining said face paper weight includes dividing said face paper stiffness value by a Tensile Stiffness Index Area (TSIA) value.

8. The method of claim 7, wherein said TSIA value is in the range of 12 to 20 kNm/g.

9. The method of claim 6, wherein said core strength value is in the approximate range of 400 to 500 psi.

* * * * *